(12) United States Patent
Schaible

(10) Patent No.: US 9,592,002 B2
(45) Date of Patent: Mar. 14, 2017

(54) METHOD AND SYSTEM TO DERIVE MULTIPLE GLYCEMIC PATTERNS FROM GLUCOSE MEASUREMENTS DURING TIME OF THE DAY

(71) Applicant: LifeScan, Inc., Milpitas, CA (US)

(72) Inventor: Thomas Schaible, Phoenixville, PA (US)

(73) Assignee: LifeScan, Inc., Wayne, PA (US)

( * ) Notice: Subject to any disclaimer, the term of this patent is extended or adjusted under 35 U.S.C. 154(b) by 768 days.

(21) Appl. No.: 13/624,733

(22) Filed: Sep. 21, 2012

(65) Prior Publication Data

US 2014/0083867 A1    Mar. 27, 2014

(51) Int. Cl.
*G06F 19/18* (2011.01)
*G06F 19/22* (2011.01)
*G06F 19/16* (2011.01)
*A61B 5/1486* (2006.01)
*G06F 19/00* (2011.01)
*A61B 5/145* (2006.01)
*A61B 5/00* (2006.01)

(52) U.S. Cl.
CPC ........ *A61B 5/1486* (2013.01); *A61B 5/14532* (2013.01); *A61B 5/7275* (2013.01); *G06F 19/345* (2013.01); *A61B 5/0022* (2013.01)

(58) Field of Classification Search
None
See application file for complete search history.

(56) References Cited

U.S. PATENT DOCUMENTS

| | | |
|---|---|---|
| 7,276,029 B2 | 10/2007 | Goode, Jr. et al. |
| 2008/0234992 A1 | 9/2008 | Ray et al. |
| 2008/0312512 A1 | 12/2008 | Brukalo et al. |
| 2010/0332445 A1 | 12/2010 | Ray et al. |
| 2011/0205064 A1 | 8/2011 | Strachan et al. |

*Primary Examiner* — Larry D Riggs, II

(57) ABSTRACT

Described are methods and systems for determining modal patterns from an overall trend, minor trend or significant trend for various periods during a time of the day modal report which can be utilized to provide insights to the person with diabetes.

19 Claims, 3 Drawing Sheets

METHOD AND SYSTEM TO DERIVE MULTIPLE GLYCEMIC PATTERNS FROM GLUCOSE MEASUREMENTS DURING TIME OF THE DAY

BACKGROUND

Diabetes mellitus is a chronic metabolic disorder caused by an inability of the pancreas to produce sufficient amounts of insulin so that the subject metabolism is unable to provide for the proper absorption of sugar and starch. This failure leads to hyperglycemia, i.e. the presence of an excessive amount of analyte within the blood plasma. Persistent hyperglycemia has been associated with a variety of serious symptoms and life threatening long term complications such as dehydration, ketoacidosis, diabetic coma, cardiovascular diseases, chronic renal failure, retinal damage and nerve damages with the risk of amputation of extremities. Because healing is not yet possible, a permanent therapy is necessary which provides constant glycemic control in order to always maintain the level of blood analyte within normal limits. Such glycemic control is achieved by regularly supplying external drugs to the body of the patient to thereby reduce the elevated levels of blood analyte.

An external biologically effective drug (e.g., insulin or its analog) was commonly administered by means of multiple, daily injections of a mixture of rapid and intermediate acting drug via a hypodermic syringe. While this treatment does not require the frequent estimation of blood analyte, it has been found that the degree of glycemic control achievable in this way is suboptimal because the delivery is unlike physiological drug production, according to which drug(s) enters the bloodstream at a lower rate and over a more extended period of time. Improved glycemic control may be achieved by the so-called intensive drug therapy which is based on multiple daily injections, including one or two injections per day of a long acting drug for providing basal drug and additional injections of a rapidly acting drug before each meal in an amount proportional to the size of the meal. Although traditional syringes have at least partly been replaced by drug pens, the frequent injections are nevertheless very inconvenient for the patient, particularly those who are incapable of reliably self-administering injections.

Substantial improvements in diabetes therapy have been achieved by the development of the drug delivery device, relieving the patient of the need for syringes or drug pens and the administration of multiple, daily injections. The drug delivery device allows for the delivery of a drug in a manner that bears greater similarity to the naturally occurring physiological processes and can be controlled to follow standard or individually modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Drug delivery devices have been utilized to assist in the management of diabetes by infusing drug or a suitable biologically effective material into the diabetic patient at a basal rate with additional drug or "bolus" to account for meals or high analyte values, levels or concentrations. The drug delivery device is connected to an infuser, better known as an infusion set by a flexible hose. The infuser typically has a subcutaneous cannula, adhesive backed mount on which the cannula is attached thereto. The cannula may include a quick disconnect to allow the cannula and mount to remain in place on the skin surface of the user while the flexible tubing is disconnected from the infuser. Regardless of the type of drug delivery device, blood analyte monitoring is required to achieve acceptable glycemic control. For example, delivery of suitable amounts of drug by the drug delivery device requires that the patient frequently determines his or her blood analyte level and manually input this value into a user interface for the external pumps, which then calculates a suitable modification to the default or currently in-use drug delivery protocol, i.e. dosage and timing, and subsequently communicates with the drug delivery device to adjust its operation accordingly. The determination of blood analyte concentration is typically performed by means of an episodic measuring device such as a handheld electronic meter which receives blood samples via enzyme-based test strips and calculates the blood analyte value based on the enzymatic reaction.

In recent years, continuous analyte monitoring has also been utilized with drug delivery devices to allow for greater control of the drug(s) being infused into the diabetic patients. In addition to glucose monitoring, people with diabetes often have to perform drug therapy such as, for example, insulin dosing. People with diabetes may self-administer insulin to reduce their glucose concentration. There are a number of mechanical devices currently available which enable an individual to dose a predetermined quantity of insulin such as, for example, a hypodermic syringe, an insulin pen, and an insulin pump. One such insulin pump is the Animas® Ping, a product which is manufactured by Animas Corporation. Another is the Animas® Vibe, also manufactured by Animas Corporation.

People with diabetes should maintain tight control over their lifestyle, so that they are not adversely affected by, for example, irregular food consumption or exercise. In addition, a physician dealing with a particular individual with diabetes may require detailed information on the individual's lifestyle to provide effective treatment or modification of treatment for controlling diabetes. Currently, one of the ways of monitoring the lifestyle of an individual with diabetes has been for the individual to keep a paper logbook of their lifestyle. Another way is for an individual to simply rely on remembering facts about their lifestyle and then relay these details to their physician on each visit.

The aforementioned methods of recording lifestyle information are inherently difficult, time consuming, and possibly inaccurate. Paper logbooks are not necessarily always carried by an individual and may not be accurately completed when required. Such paper logbooks are small and it is therefore difficult to enter detailed information requiring detailed descriptors of lifestyle events. Furthermore, an individual may often forget key facts about their lifestyle when questioned by a physician who has to manually review and interpret information from a hand-written notebook. There is no analysis provided by the paper logbook to distill or separate the component information. Also, there are no graphical reductions or summary of the information. Entry of data into a secondary data storage system, such as a database or other electronic system, requires a laborious transcription of information, including lifestyle data, into this secondary data storage. Difficulty of data recordation encourages retrospective entry of pertinent information that results in inaccurate and incomplete records.

Recognizing these deficiencies, LifeScan Inc., has invented a diabetes management technique that utilizes statistical analyses, for example, a chi-squared test, to ensure the robustness of the glucose measurements. The technique is shown and described in U.S. patent application Ser. No. 11/688,639, now allowed, which is hereby incorporated by reference into this application as if fully set forth herein.

SUMMARY OF THE DISCLOSURE

Applicant has discovered that in certain situations, such as during various time periods during a day, it is sufficient to utilize an overall trend along with a minor trend without resorting to statistical analysis in order to detect patterns that occur during these various periods in the time of the day. Applicant has also further discovered that by combining an overall trend with a chi-squared test, this has allowed applicant to use much lower significance values in the chi-squared test while still obtaining patterns that are insightful for the subject during various periods during a time of the day. Essentially, the "overall" trend, as an additional check, protects against any "weak signals" that the chi-squared test on its own would report to the user, thereby maintaining the robustness of the pattern detection technique.

In one aspect, a system for management of diabetes of a subject is provided. The system includes at least one glucose monitor and a controller. The at least one glucose monitor is configured to measure a glucose concentration based on an enzymatic reaction with physiological fluid in a biosensor that provides an electrical signal representative of the glucose concentration. The controller is in communication with at least one glucose monitor, the controller being configured to receive or transmit glucose data representative of glucose levels measured by the glucose monitor over a predetermined time period to determine whether the glucose data includes at least one of: (a) an overall trend having: (1) a minimum number of glucose measurements; (2) a minimum number of glucose measurements that have values above a target range, below a target range, or in-range category in the time slot; and (3) the percentage of glucose measurements in the timeslot being greater than a minimum threshold; (b) a minor trend having a minimum number of glucose measurements within a specified number of days that have values above a target range, below a target range, or in-range category in the time slot and all of the glucose measurements in the minimum number must be within a specified number of hours of each other; and the controller, upon determination of one of the overall trend and minor trend, annunciate to the subject such determination.

In another aspect, a method of determining at least one of certain trends in a time of day for glucose measurements with at least one glucose monitor and a controller. The controller is in communication with the at least one glucose monitor. The controller may include a microprocessor and be configured to receive or transmit glucose data representative of glucose levels measured by the glucose monitor. The method can be achieved by: performing a plurality of glucose measurements over a predetermined time period with the glucose monitor; identifying, with the microprocessor, from the plurality of glucose measurements one of: (a) an overall trend having: (1) a minimum number of glucose measurements; (2) a minimum number of glucose measurements that have values in the above a target range, below a target range, or in-range category in the time slot; and (3) the percentage of glucose measurements in the timeslot being greater than a minimum threshold; (b) a significant trend in which such significant trend is statistically and significantly different than the trends observed in other timeslots and a chi-squared test is used to determine if a particular time slot of the time slots is statistically significantly different than other time slots, the statistical test being based on a percentage of hypoglycemic incidence per the time slot interval and a predicted percentage of hypoglycemic incidence per the time slot interval; and in the event the identifying step indicates one of (a) or (b), annunciating such identification to the subject.

In each of the above aspects, the following features can be combined with each aspect alone or in combination with other aspects set forth herein. For example, the minimum number of glucose measurements may include about 14 measurements; the minimum number of glucose measurements in one of the in-range, above a target range or below a target range may include about two for measurements below a target range, about three measurements above a target range, 4 measurements that are within the target range; and the minimum threshold may include about 50% of the measurements being above a target range, 5% of the measurements being below the target range, 70% being within the target range; the minimum number of glucose measurements of a minor trend may include about two for measurements below a target range, about three measurements above a target range, about seven measurements that are within the target range and the specified number of hours may include about 3 hours; the controller is configured to determine a significant trend in which such significant trend is statistically and significantly different than the trends observed in other timeslots and a chi-squared test is used to determine if a particular time slot of the time slots is statistically significantly different than other time slots; the statistical test being based on a percentage of hypoglycemic incidence per the time slot interval and a predicted percentage of hypoglycemic incidence per the time slot interval, and the controller is configured to annunciate that a significant trend has been detected in the particular time slot; the chi-squared test utilizes a confidence level ranging from about 90% to about 99%; the controller is configured to: calculate a chi-squared $\chi^2$ using the following equation:

$$\chi^2 = \sum_{i=1}^{n} \frac{(L_i - L_{i,pre})^2}{L_{i,pre}} + \sum_{i=1}^{n} \frac{(L'_i - L'_{i,pre})^2}{L'_{i,pre}}$$

where $\chi^2$=chi-squared, i represents a particular time slot interval, n is a total number of time slot intervals, $L_i$ is a number of substantially hypoglycemic glucose concentration measurements that occur during time slot interval i, $L_{i,pre}$ is a predicted number of substantially hypoglycemic glucose concentration measurements that will occur during time slot interval i, and $L_{i,pre}'$ is a predicted number of non-hypoglycemic glucose concentration measurements that will occur interval time i; compare the calculated $\chi^2$ to a $\chi^2$ value in a table based on a number of degrees of freedom for each of the time slot intervals i; determine that at least one of the time slot intervals are statistically significantly different if the calculated $\chi^2$ is greater than the $\chi^2$ value of the table; and calculating $L_{i,pre}$ and $L_{i,pre}'$ using estimation equations may include:

$$L_{i,pre} = \frac{\sum_{i=1}^{n} L_i}{\sum_{i=1}^{n} N_i} * N_i$$

and $$L'_{i,pre} = \frac{\sum_{i=1}^{n} L'_i}{\sum_{i=1}^{n} N_i} * N_i$$

where $N_i$ represents the total number of glucose concentration measurements performed during time interval i.

In each of the above aspects, the following features can be combined with each aspect alone or in combination with other aspects set forth herein. For example, the controller is further configured to: identify one of the time slot intervals as being statistically significantly different with a Z test; the controller is further configured to: calculate $Z_i$ using a Z test, the Z test may include:

$$Z_i = \frac{(L_i - L_{i,pre})}{SE_i}$$

where $Z_i$ represents a Z test at a particular time slot interval i and $SE_i$ represents a standard error for a particular time slot interval i;
compare a calculated $Z_i$ to a Z value in a table; identify that one of the time slot intervals is statistically significantly different if the calculated $Z_i$ is greater than the Z test; and annunciate the one of the time slot intervals; the Z test includes a threshold of about one to about two; the controller is configured to: calculate $SE_i$, using a standard error equation may include:

$$SE_i = \sqrt{\frac{1}{N_i} * L_{i,pre} * (N_i - L_{i,pre})}$$

In each of the above aspects, the following features can be combined with each aspect alone or in combination with other aspects set forth herein. For example, a chi-squared test is used to determine if any of the time slots is statistically significantly different from other time slots; the chi-squared test may include a confidence level of about 90%; the number of glucose measurements is greater than about 14; the technique may include calculating a chi-squared $\chi^2$ using the following:

$$\chi^2 = \sum_{i=1}^{n} \frac{(L_i - L_{i,pre})^2}{L_{i,pre}} + \sum_{i=1}^{n} \frac{(L'_i - L'_{i,pre})^2}{L'_{i,pre}}$$

where $\chi^2$=chi-squared, i represents a particular time slot interval, n is a total number of time slot intervals, $L_i$ is a number of substantially hypoglycemic glucose concentration measurements that occur during time slot interval i, $L_{i,pre}$ is a predicted number of substantially hypoglycemic glucose concentration measurements that will occur during time slot interval i, and $L_{i,pre}'$ is a predicted number of non-hypoglycemic glucose concentration measurements that will occur interval time i;
comparing a calculated $\chi^2$ to a $\chi^2$ value in a table based on a number of degrees of freedom for each of the time slot intervals i; and
determining that at least one of the time slot intervals are statistically significantly different if the calculated $\chi^2$ is greater than the $\chi^2$ value on the table.

In each of the above aspects, the following features can be combined with each aspect alone or in combination with other aspects set forth herein. For example, calculating $L_{i,pre}$ and $L_{i,pre}'$ using estimation equations may include:

$$L_{i,pre} = \frac{\sum_{i=1}^{n} L_i}{\sum_{i=1}^{n} N_i} * N_i$$

and $$L'_{i,pre} = \frac{\sum_{i=1}^{n} L'_i}{\sum_{i=1}^{n} N_i} * N_i$$

where $N_i$ represents the total number of glucose concentration measurements performed during time interval i.

In each of the above aspects, the following features can be combined with each aspect alone or in combination with other aspects set forth herein. For example, identifying one of the time slot intervals as being statistically significantly different using a Z test; the Z test may include:

$$Z_i = \frac{(L_i - L_{i,pre})}{SE_i}$$

where $Z_i$ represents a Z test at a particular time slot interval i and $SE_i$ represents a standard error for a particular time slot interval i; and further may include: comparing a calculated $Z_i$ to a Z value in a table; and identifying that one of the time slot intervals is statistically significantly different if the calculated $Z_i$ is greater than the Z test.

In each of the above aspects, the following features can be combined with each aspect alone or in combination with other aspects set forth herein. For example, the Z test includes a threshold of about one and calculating $SE_i$, using a standard error equation may include:

$$SE_i = \sqrt{\frac{1}{N_i} * L_{i,pre} * (N_i - L_{i,pre})} \, .$$

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include pharmaceuticals or other chemicals that causes a biological response in the body of a user or patient.

Figure 1:
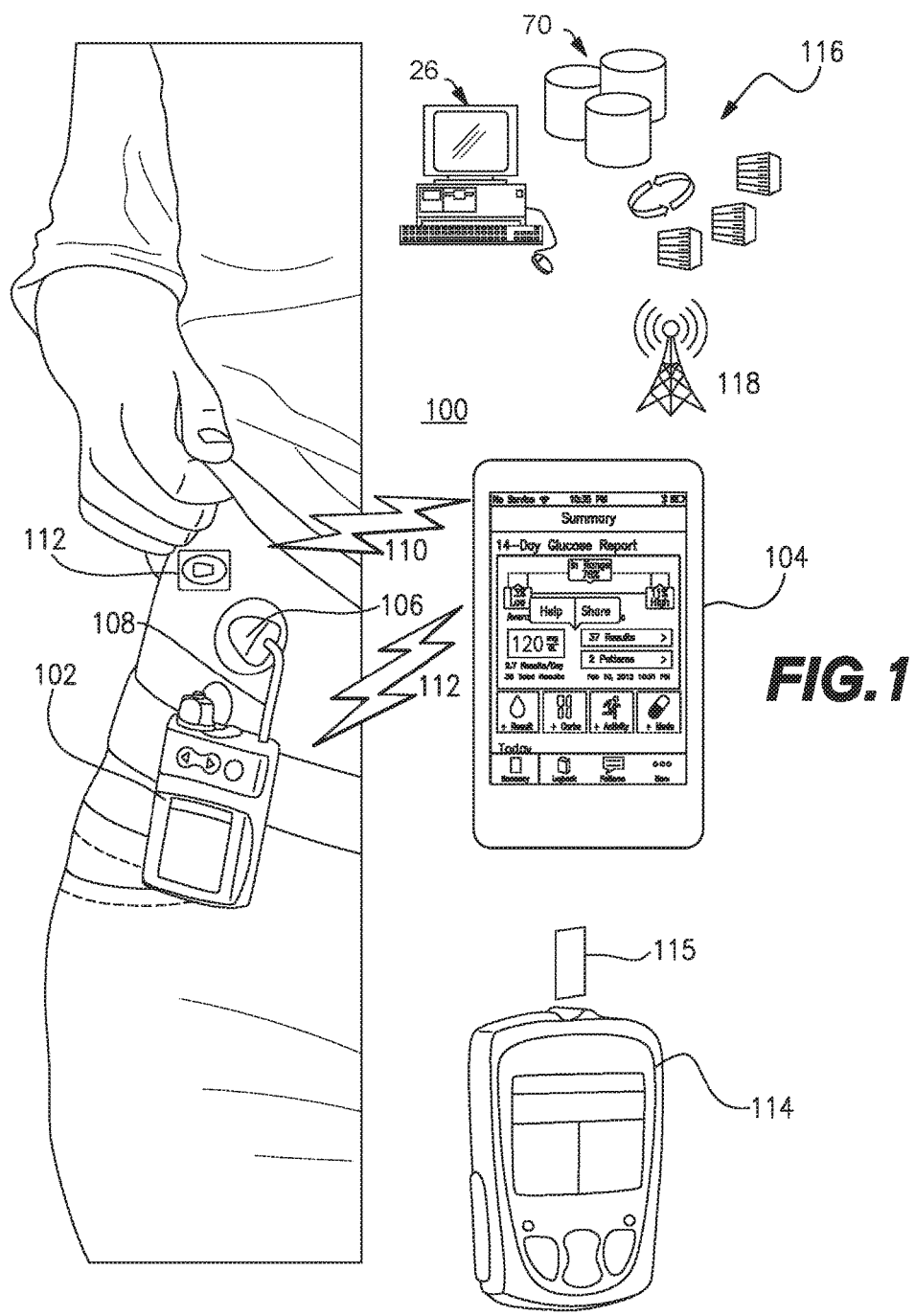
FIG. 1 illustrates an exemplary embodiment of the diabetic management system.

FIG. 1 illustrates a drug delivery system 100 according to an exemplary embodiment. Drug delivery system 100 includes a drug delivery device 102 and a remote controller 104. Drug delivery device 102 is connected to an infusion set 106 via flexible tubing 108.

Drug delivery device 102 is configured to transmit and receive data to and from remote controller 104 by, for example, radio frequency communication 110. Drug delivery device 102 may also function as a stand-alone device with its own built in controller. In one embodiment, drug delivery device 102 is a drug infusion device and remote controller 104 is a hand-held portable controller. In such an embodiment, data transmitted from drug delivery device 102 to remote controller 104 may include information such as, for example, drug delivery data, glucose information, basal, bolus, insulin to carbohydrates ratio or insulin sensitivity factor, to name a few. The controller 104 may be configured to receive continuous analyte readings from a continuous analyte ("CGM") sensor 112. Data transmitted from remote controller 104 to drug delivery device 102 may include analyte test results and a food database to allow the drug delivery device 102 to calculate the amount of drug to be delivered by drug delivery device 102. Alternatively, the remote controller 104 may perform dosing or bolus calculation and send the results of such calculations to the drug delivery device. In an alternative embodiment, an episodic blood analyte meter 114 may be used alone or in conjunction with the CGM sensor 112 to provide data to either or both of the controller 102 and drug delivery device 102. Alternatively, the remote controller 104 may be combined with the meter 114 into either (a) an integrated monolithic device; or (b) two separable devices that are dockable with each other to form an integrated device. Each of the devices 102, 104, and 114 has a suitable micro-controller (not shown for brevity) programmed to carry out various functionalities. For example, a microcontroller can be in the form of a mixed signal microprocessor (MSP) for each of the devices 102, 104, or 114. Such MSP may be, for example, the Texas Instrument MSP 430, as described in U.S. Patent Application Publication numbers US2010-0332445, and US2008-0312512 which are incorporated by reference in their entirety herein to this application. The MSP 430 or the pre-existing microprocessor of each of these devices can be configured to also perform the method described and illustrated herein.

The measurement of glucose can be based on a physical transformation (i.e., the selective oxidation) of glucose by the enzyme glucose oxidase (GO). For example, in the strip type biosensor, the reactions that can occur in such biosensor are summarized below in Equations 1a and 1b.

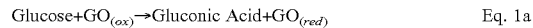

$$\text{Glucose} + \text{GO}_{(ox)} \rightarrow \text{Gluconic Acid} + \text{GO}_{(red)} \qquad \text{Eq. 1a}$$

$$\text{GO}_{(red)} + 2\text{Fe(CN)}_6^{3-} \rightarrow \text{GO}_{(ox)} + 2\text{Fe(CN)}_6^{4-} \qquad \text{Eq. 1b}$$

As illustrated in Equation 1a, glucose is oxidized to gluconic acid by the oxidized form of glucose oxidase $(\text{GO}_{(ox)})$. It should be noted that $\text{GO}_{(ox)}$ may also be referred to as an "oxidized enzyme." During the chemical reaction in Equation 1a, the oxidized enzyme $\text{GO}_{(ox)}$ is transformed to its reduced state, which is denoted as $\text{GO}_{(red)}$ (i.e., "reduced enzyme"). Next, the reduced enzyme $\text{GO}_{(red)}$ is i re-oxidized back to $\text{GO}_{(ox)}$ by reaction with $\text{Fe(CN)}_6^{3-}$ (referred to as either the oxidized mediator or ferricyanide) as illustrated in Equation 1b. During the re-generation or transformation of $\text{GO}_{(red)}$ back to its oxidized state $\text{GO}_{(ox)}$, $\text{Fe(CN)}_6^{3-}$ is reduced to $\text{Fe(CN)}_6^{4-}$ (referred to as either reduced mediator or ferrocyanide).

When the reactions set forth above are conducted with a test voltage applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose current.

Analyte levels or concentrations can also be determined by the use of the CGM sensor 112. The CGM sensor 112 utilizes amperometric electrochemical sensor technology to measure analyte with three electrodes operably connected to the sensor electronics and are covered by a sensing membrane and a biointerface membrane, which are attached by a clip.

The top ends of the electrodes are in contact with an electrolyte phase (not shown), which may include a free-flowing fluid phase disposed between the sensing membrane and the electrodes. The sensing membrane may include an enzyme, e.g., analyte oxidase, which covers the electrolyte phase. In this exemplary sensor, the counter electrode is provided to balance the current generated by the species being measured at the working electrode. In the case of an analyte oxidase based glucose sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of glucose in the user's body, and therefore may be utilized to estimate a meaningful glucose value. Details of the sensor and associated components are shown and described in U.S. Pat. No. 7,276,029, which is incorporated by reference herein as if fully set forth herein this application. In one embodiment, a continuous analyte sensor from the Dexcom Seven System (manufactured by Dexcom Inc.) can also be utilized with the exemplary embodiments described herein.

Drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from drug delivery device 102. Examples of remote monitoring station 116 may include, but are not limited to, a personal or networked computer, a personal digital assistant, other mobile telephone, a hospital base monitoring station or a dedicated remote clinical monitoring station.

Drug delivery device 102 includes processing electronics including a central processing unit and memory elements for storing control programs and operation data, a radio frequency module 116 for sending and receiving communication signals (i.e., messages) to/from remote controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing a drug from a drug reservoir (e.g., a drug cartridge) through a side port connected to an infusion set 106 and into the body of the user.

The components of the system described in relation to FIG. 1 are helpful to the person with diabetes in managing their disease. However, to achieve the efficacy in management of the disease, the person with diabetes would need more than just these components. As applicant has recognized, the component or the system must be able to provide easy to understand information that assist in the decision making of the person. To assist in this, applicant has devised a system that provides insights into the glucose measurements obtained for management of diabetes of a subject.

Figure 2:
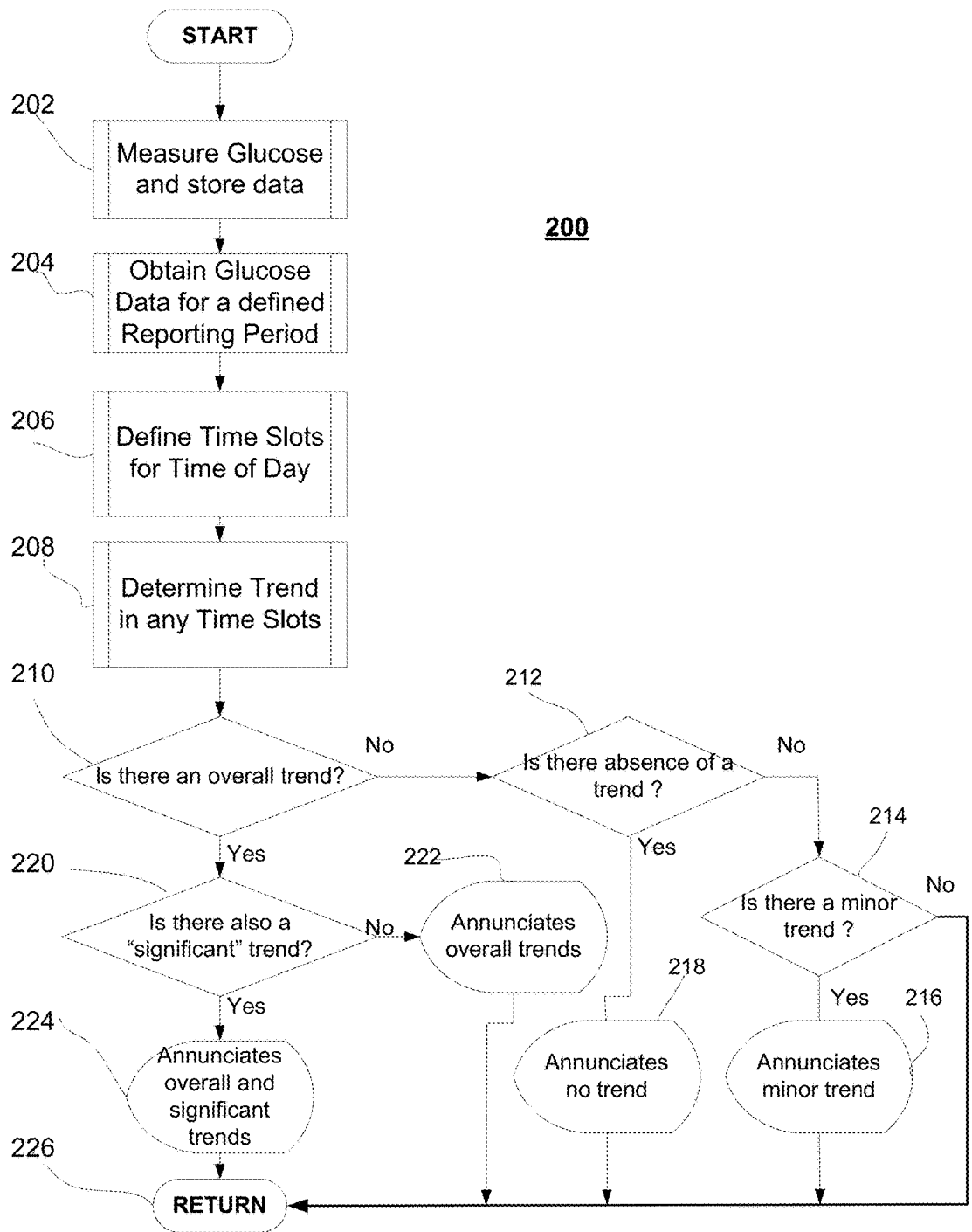
FIG. 2 illustrates an exemplary logic 200 of the technique utilized by the system of FIG. 1.

For the system of FIG. 1 to operate in accordance with applicant's new technique, a controller 104 is set up to be in communication with at least one glucose monitor (SMBG, CGM, or both). The controller 104 is configured to receive or transmit glucose data representative of glucose levels measured by the glucose monitor over a predetermined time period. By doing this, the controller, in accordance with the logic 200 of FIG. 2, is able to determine clusters of glucose data with respect to glucose levels and the predetermined time so that the glucose levels with reference to a predetermined time period are correlated to each other in a cluster due to their similarity as compared to glucose levels in other clusters.

In particular, the logic 200 begins with measurements of glucose data with the glucose monitor at step 202. The glucose data may include more than just the glucose concentration such as, for example, date, time, user's flags and other suitable records related to diabetes. For brevity, the discussion will use glucose data but it should be clear that the embodiments herein are not limited to solely glucose measurements.

At step 204, the number of glucose data collected is obtained for a defined reporting time period, such as, for example, 3-day, 7-day, 14-day, 21-day, 30-day, 45-day, 90-day or any time period defined by the user. At step 206, a patient or user may configure the software system with Time of Day timeslots. A timeslot is defined as a start time and end time within a day. The system allows for any number of timeslots, but the timeslots must span a complete day. For example, the patient may configure the system with three timeslots, one timeslot at 12:00 AM-8:00 AM, a second time slot at 8:00 AM-2:00 PM, and a third time slot at 2:00 PM-12:00 AM.

Steps 210-224 are designed to evaluate for overall trend, significant trend, minor trend, or the absence of a trend in any time slot. An overall trend may be a trend that is below a target glucose range, above the target glucose range, or a trend that is in-range of the target glucose range. For a timeslot to exhibit an overall trend in step 210, all of the following criteria must be met: (a) The entire data set must contain a minimum number of glucose measurements designated as "Overall-Trend-Minimum-Number-Of-Glucose-Data"; (b) the timeslot must contain a minimum number of glucose measurements that have values in the above a target range, below a target range, or in-range category. This number is designated as "Overall-Trend-Minimum-Number-Of-Glucose-Data-In-Specified-Category"; and (c) the percentage of glucose measurements in the timeslot that have values in the above a target range, below a target range, or in-range category must be greater than a minimum threshold defined as "Overall-Trend-Minimum-Percentage-Of-Glucose-Data."

As an example of a determination of an overall trend for the 12:00 AM-8:00 AM timeslot, logic may check the following parameters for an above a target range trend: (a) The entire data set must contain from about 14 to about 28 glucose measurement points to be included in the Overall-Trend-Minimum-Number-Of-Glucose-Data; (b) at least 3 glucose readings or measurements are above a target range in the 12:00 AM-8:00 AM timeslot and therefore these readings are placed in the Overall-Trend-Minimum-Number-Of-Glucose-Data-In-Specified-Category; and (c) at least 50% of readings are above a target range in the 12:00 AM-8:00 AM timeslot in order to be included in the Overall-Trend-Minimum-Percentage-Of-Glucose-Data. Overall trends will only be determined in step 210 (and returned as a yes in step 210) if less than 50% of the timeslots had a trend present. If greater than 50% of the timeslots had a trend present, then there would be no specific trend by timeslot, but rather an overarching trend.

If the logic in step 210 indicates that there is no overall trend (returning a "no" in step 210) then the logic 200 checks to determine if there is an absence of any trend. If the query in step 212 confirms that there is no trend detected a time interval in a day, the system will annunciate the same in step 218. On the other hand, if the query in step 212 indicates that there is a trend other than an overall trend, then another query in step 214 is utilized to determine if this trend is a minor trend or not. If the query in step 214 returns an indication of no minor trend then the system will return to the main system routine 226.

For a determination of a minor trend in step 214, all of the following criteria must be met: (a) the data set must contain a minimum number of glucose measurements within a specified number of days that have values in the in-range, above a target range, or below a target range categories and all of the glucose measurements in the minimum number must be within a specified number of hours of each other; (b) the minimum number of glucose measurements have been obtained by the system and referenced as "Minor-Trend-Minimum-Number-Of-Glucose-Data"; (c) the specified number of days have been defined and referenced as "Minor-Trend-Day-Span"; (d) the specified number of hours have been defined and referenced as "Minor-Trend-Hour-Span". It is noted that multiple minor trends may be present in the data.

As an example, the logic 200 will check the following parameters for the below a target range minor trend. Upon checking, it can be determined that the dataset contains 2 below a target range readings within 3 days that are within +/−3 hours of each other. Consequently, the system will report that the data in the predetermined time period for reporting contain "minor" trends. A minor trend can be displayed in text form with a message noting the trend and time, such as "You have an above a target range trend between 1:00 and 3:00". Alternatively, a minor trend can be displayed visually by connecting glucose measurements together with lines or circling the points involved in the trend. One illustrative example is shown as a minor trend 304 in FIG. 3. Details of the technique to determine the minor trend can be found in U.S. patent application Ser. No. 12/826,543 (published as US Patent Application Publication No. US-2011-0205064-A) to ANALYTE TESTING METHOD AND SYSTEM WITH HIGH AND LOW BLOOD GLUCOSE TRENDS NOTIFICATION, which patent application is incorporated by reference into this application as if fully set forth herein.

Referring back to step 210, where it may be determined that there was an overall trend then in such case, a determination is made in query 220 if the overall trend also includes a "significant" trend and if step 220 returns a "no" then the system will annunciate the overall trend(s) without inclusion of any "significant" trend. One example of an overall trend is shown at 302 in FIG. 3.

For a determination of a "significant" trend in step 220, i.e., a trend that is statistically significantly different than the trends observed in other timeslots, the logic of the system will construct a chi-square table to quantify the significance of the trends in the data. In the example here, the significance will be correlated to two specific outcomes: hypoglycemia (where the glucose reading is below a specified value or range) or hyperglycemia (where the glucose is above a specified value or range). Specifically, the system begins by listing the count of observed glucose readings for each timeslot that were in the selected category (in-range, above a target range, below a target range) and not in the selected category. In the chi-square table (e.g., Table I below) an expected value will be constructed based upon the overall distribution of readings that are "in" a category and "not in" the category and the number of glucose measurements in the given timeslot. Significance in this case is evidence that, based upon the data categorized by timeslots, there is significant evidence that glucose records in one or more timeslots differ from the larger population of glucose records. That is, significance indicates that there is evidence that the population of glucose records in one or more timeslots is different in some way from the overall population of glucose records. This is calculated based upon the chi-squared value being above a threshold defined by the desired confidence. The confidence level (e.g., 90%, 95%, 99%, etc.) is pre-chosen, and based upon the number of timeslots analyzed (which drives the degrees of freedom) the threshold chi-squared value can be identified.

For a timeslot to exhibit a significant trend, all of the following criteria must be met: (a) The entire data set must contain a minimum number of glucose measurements defined as "Minimum-Significant-Trend-Glucose-Data"; (b) 80% of the expected values in each cell in the chi-square table must be greater than a threshold defined as "Significant-Trend-Expected-Value-Threshold"; (c) A chi-square analysis of the table (e.g., Table I) must produce a confidence level greater than a threshold defined as "Significant-Trend-Confidence"; and (d) the timeslot must exhibit a significant difference as measured by a Z-Value greater than a threshold defined as "Significant-Trend-Z". It is noted that multiple significant trends may be present, but they will only be reported when they are also paired with an overall trend.

In one embodiment, the Z test may be a two-sided Z test. In this test, the calculated $Z_i$ value is compared to a value of about 2. If the calculated $Z_i$ is greater than about 2, then a flag (or message) indicating a high incidence of hypoglycemia has occurred at a particular time slot will be stored in memory.

The chi-squared test may use a confidence level or Significant-Trend-Confidence ranging from about 90% to about 99%. Equation 2 shows an example of how to calculate chi-squared $\chi^2$.

$$\chi^2 = \sum_{i=1}^{n} \frac{(L_i - L_{i,pre})^2}{L_{i \cdot pre}} + \sum_{i=1}^{n} \frac{(L'_i - L'_{i,pre})^2}{L'_{i \cdot pre}} \qquad \text{Eq. 3}$$

TABLE I

| | Outcome 1 (e.g. Hypoglycemic) | | Outcome 2 (e.g., Not Hypoglycemic) | | Row Total | SE (Standard Error) | Z test |
| --- | --- | --- | --- | --- | --- | --- | --- |
| | Observed | Expected | Observed | Expected | | | |
| Condition 1 (e.g., time of the day) | $L_1$ | $L_{1,pre} = \frac{\sum_{i=1}^{n} L_i}{\sum_{i=1}^{n} N_i} * N_1$ | $\acute{L}_1$ | $L'_{1,pre} = \frac{\sum_{i=1}^{n} L'_i}{\sum_{i=1}^{n} N_i} * N_1$ | $N_1 = L_1 + \acute{L}_1$ | $SE_1 = \sqrt{\frac{1}{N_1} * L_{1,pre} * (N_1 - L_{1,pre})}$ | $Z_1 = \frac{(L_1 - L_{1,pre})}{SE_1}$ |
| Condition 2 | $L_2$ | $L_{2,pre} = \frac{\sum_{i=1}^{n} L_i}{\sum_{i=1}^{n} N_i} * N_2$ | $\acute{L}_2$ | $L'_{2,pre} = \frac{\sum_{i=1}^{n} L'_i}{\sum_{i=1}^{n} N_i} * N_2$ | $N_2 = L_2 + \acute{L}_1$ | $SE_2 = \sqrt{\frac{1}{N_2} * L_{2,pre} * (N_2 - L_{2,pre})}$ | $Z_2 = \frac{(L_2 - L_{2,pre})}{SE_2}$ |
| Condition 3 | $L_3$ | $L_{3,pre} = \frac{\sum_{i=1}^{n} L_i}{\sum_{i=1}^{n} N_i} * N_3$ | $\acute{L}_3$ | $L'_{3,pre} = \frac{\sum_{i=1}^{n} L'_i}{\sum_{i=1}^{n} N_i} * N_3$ | $N_3 = L_3 + \acute{L}_3$ | $SE_3 = \sqrt{\frac{1}{N_3} * L_{3,pre} * (N_3 - L_{3,pre})}$ | $Z_3 = \frac{(L_3 - L_{3,pre})}{SE_3}$ |
| ... | ... | ... | ... | ... | ... | ... | ... |
| Condition n | $L_n$ | $L_{n,pre} = \frac{\sum_{i=1}^{n} L_i}{\sum_{i=1}^{n} N_i} * N_n$ | $\acute{L}_n$ | $L'_{n,pre} = \frac{\sum_{i=1}^{n} L'_i}{\sum_{i=1}^{n} N_i} * N_n$ | $N_n = L_n + \acute{L}_n$ | $SE_n = \sqrt{\frac{1}{N_n} * L_{n,pre} * (N_n - L_{n,pre})}$ | $Z_n = \frac{(L_n - L_{n,pre})}{SE_n}$ |

In Equation 2, the term $L_i'$ is a number of non-hypoglycemic glucose concentration measurements that occur during time slot interval i. $L_{i,pre}$ is a predicted number of substantially hypoglycemic glucose concentration measurements that will occur during time slot interval i. $L_{i,pre}'$ is a predicted number of non-hypoglycemic glucose concentration measurements that will occur during time slot interval i. After determining $\chi^2$ using Equation 2, the calculated $\chi^2$ value is compared to a $\chi^2$ in a table based on a number of degrees of freedom for each of the time slot intervals i. If the calculated $\chi^2$ is greater than the $\chi^2$ value on the table, then at least one of the time slot intervals is statistically significantly different.

The term $L_{i,pre}$ may be calculated using Equation 3a.

$$L_{i,pre} = \frac{\sum_{i=1}^{n} L_i}{\sum_{i=1}^{n} N_i} * N_i \qquad \text{Eq. 3a}$$

The term $L_{i,pre}'$ may be calculated using Equation 3b.

$$L'_{i,pre} = \frac{\sum_{i=1}^{n} L'_i}{\sum_{i=1}^{n} N_i} * N_i \qquad \text{Eq. 3b}$$

The term $$\frac{\sum_{i=1}^{n} L_i}{\sum_{i=1}^{n} N_i}$$

represents a fraction that estimates the likelihood of observing a hypoglycemic event based on all of the recurring time slot intervals combined.

The technique to determine "significant" trend in hypoglycemia or hyperglycemia may further include identifying which one of the recurring time slot intervals i is statistically significantly different using a Z test if the chi-squared test determines that at least one of the time slot intervals is statistically significantly different. Equation 4 shows an example of the Z test.

$$Z_i = \frac{(L_i - L_{i,pre})}{SE_i} \qquad \text{Eq. 4}$$

The term $Z_{i\ or}$ Significant-Trend-Z represents a Z value at a particular time slot interval and $SE_i$ represents a standard error for a particular time slot interval i. The term $SE_i$ may be calculated using Equation 5.

$$SE_i = \sqrt{\frac{1}{N_i} * L_{i,pre} * (N_i - L_{i,pre})} \qquad \text{Eq. 5}$$

A $Z_i$ value (e.g., the Significant-Trend-Z) may be calculated for each recurring time slot interval i and compared to a Z value in a table. If the $Z_i$ value for one of the recurring time slot intervals is greater than the Z value in the table (e.g., about two), then the particular recurring time slot interval i is statistically significantly different.

As an example, the logic may check the following parameters for the below a target range significant trend. The dataset must contain a minimum, for example, from about 14 to about 27 data points (i.e., glucose measurements). The expected value of each category in all timeslots must be greater than 5. The confidence level of chi-squared analysis must be greater than 90% and the individual timeslot must have a Significant-Trend-Z value greater than 2. In practice, however, with the combination of the overall trends, the data points, confidence, and expected values can be greatly reduced. In the preferred embodiments, the minimum number of glucose measurements are about 14 data points, where the expected value >0.5, with confidence of about 90% or higher and minimum Z is about 1. It is noted that by combining the "overall" trends with the chi-squared test has allowed the inventor to use much lower significance values in the chi-squared test while still obtaining a desirable result for the subject. Essentially, the "overall" trend, as an additional check, protects against any "weak signals" that the chi-squared test on its own would report.

The system reports all the overall trends and the significant trends that are paired with an overall trend. Significant trends that are paired with an overall trend may be described in text form noting the timeslot and trend, such as "You have an above target trend in the 12:00-6:00 timeslot that is stronger than other timeslots". One example of a significant trend indicator is shown at 306 in FIG. 3. The trend(s) may also be shown graphically by coloring the timeslot according to trend and changing the intensity of color or further outlining the timeslots to indicate the trend.

The system reports all the overall trends. Overall trends may be described in text form noting the timeslot and trend, such as "You have an above target trend in the 12:00-6:00 timeslot". Alternatively, the report can be in the form of graphical output report 300 of FIG. 3, in which the report can color the timeslots at 302 for "overall trends", 304 for "minor trends", and in 306 for "significant trends" using different color and graphical identifiers.

Figure 3:
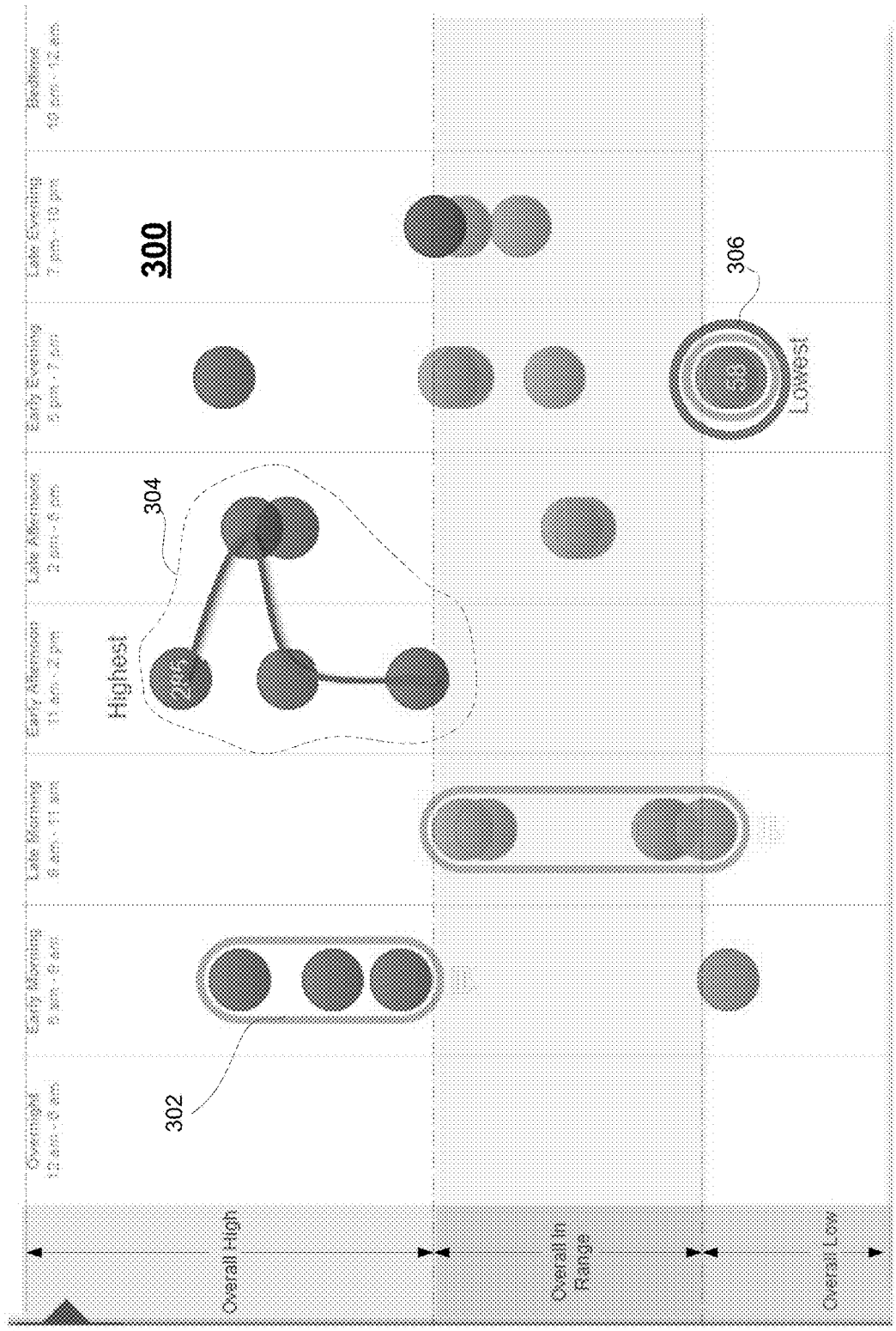
FIG. 3 illustrates an exemplary output showing the "overall trend"; "minor trend" and "significant trend" for the glucose measurements made by a subject to discern multiple patterns for periods within a time-of-the-day modal representation of glucose measurements made over multiple days.

An example of the overall trend 302 is shown in FIG. 3 at the "early morning" time-of-the-day. It is noted that when there is sufficient data to rely on a percentage for meaningful information, the system provides for identification of overall trends 302 tending toward a "high" trend which uses percentage thresholds rather than statistical significance. As a result, this technique requires far less data than is required for statistical significance. In general, most users tend to have enough data to rely on a percentage analysis, but insufficient data to rely on statistical significance. When showing these overall trends, the trends will be highlighted as shown by 302 (which can be displayed by controller 104 or a main computer 26), with the intent that they are more important than minor trends, but less important than strong or significant trends. In this case, a circle is shown around the three readings for "early morning" at the overall trend 302.

On the other hand, when there are minimal data, a minor trend can be provided. In this case, there were only 3 points in the given timeslot in the "early afternoon" of the day at minor trend 304 in FIG. 3. Because there were far too few measurements here to rely on percentages or statistical significance to distinguish them, a line may be used to link the measurements indicative of repeated high and low glucose measurements close to each other, which measurements may not be in the same time slot as "early afternoon" but also in another time slot (e.g., "late afternoon") in this example. In other words, the technique will look for repeated highs/lows "close" to each other in determining minor trends and provide them graphically such as in 304.

Finally, for significant trend 306, which are more important than minor or overall trends, the graphical output in FIG. 3 can be configured to emphasize so that these strong or significant trends are above and beyond the other trends. In this case, a double circle is used, but intensifying colors and shading can also be used.

While the invention has been described in terms of particular variations and illustrative figures, those of ordinary skill in the art will recognize that the invention is not limited to the variations or figures described. For example, the analytical utilized herein may also be used to determine the overall trend, minor trend or significant trends for day of week analysis instead of or in addition to time of the day trend analysis. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A system for management of diabetes of a subject, the system comprising:

at least one glucose monitor that is configured to measure a glucose concentration based on an enzymatic reaction with physiological fluid in a biosensor that provides an electrical signal representative of the glucose concentration; and a controller in communication with the at least one glucose monitor, the controller being configured to receive or transmit glucose data representative of glucose levels measured by the glucose monitor over a predetermined time period and to determine whether the glucose data includes or does not include:

(a) an overall trend of the glucose data, the overall trend having:
(1) a minimum number of glucose measurements;
(2) a minimum number of glucose measurements that have values in an above a target range, below a target range, or in-range category in a time slot; and
(3) a percentage of glucose measurements in the timeslot being greater than a minimum threshold;

(b) a minor trend of the glucose data, the minor trend having a minimum number of glucose measurements within a specified number of days that have values above a target range, below a target range, or in-range category in the time slot and all of the glucose measurements in the minimum number must be within a specified number of hours of each other; and (c) a significant trend of the glucose data, the significant trend having:
(1) a minimum number of glucose measurements;
(2) a chi-squared test confidence level greater than a threshold; and the controller, upon determination of the glucose data including both of the overall trend and minor trend but not the significant trend, annunciating to the subject such determination and using both of the determined overall trend and minor trend to calculate an amount of a drug to be delivered to the subject; and a drug delivery device in communication with the controller, the drug delivery device being configured to deliver the calculated amount of the drug to the subject.

2. The system of claim 1, in which the minimum number of glucose measurements comprises about 14 measurements; the minimum number of glucose measurements in one of the in-range, above a target range or below a target range comprises about two for measurements below a target range, about three measurements above a target range, 4 measurements that are within the target range; and the minimum threshold comprises about 50% of the measurements being above a target range, 5% of the measurements being below the target range, 70% being within the target range.

3. The system of claim 1, in which the minimum number of glucose measurements of a minor trend comprises about two for measurements below a target range, about three measurements above a target range, about seven measurements that are within the target range and the specified number of hours comprises about 3 hours.

4. The system of claim 1, in which the significant trend is statistically and significantly different than the trends observed in other timeslots and a chi-squared test is used to determine if a particular time slot of the time slots is statistically significantly different than other time slots; the statistical test being based on a percentage of hypoglycemic incidence per the time slot interval and a predicted percentage of hypoglycemic incidence per the time slot interval, and the controller is configured to annunciate that a significant trend has been detected in the particular time slot.

5. The system of claim 4, in which the chi-squared test utilizes a confidence level ranging from about 90% to about 99%.

6. The system of claim 4, in which the controller is configured to:
calculate a chi-squared $\chi^2$ using the following equation:

$$\chi^2 = \sum_{i=1}^{n} \frac{(L_i - L_{i,pre})^2}{L_{i,pre}} + \sum_{i=1}^{n} \frac{(L'_i - L'_{i,pre})^2}{L'_{i,pre}}$$

where $\chi^2$=chi-squared, i represents a particular time slot interval, n is a total number of time slot intervals, $L_i$ is a number of substantially hypoglycemic glucose concentration measurements that occur during time slot interval i, $L_{i,pre}$ is a predicted number of substantially hypoglycemic glucose concentration measurements that will occur during time slot interval i, and $L_{i,pre}'$ is a predicted number of non-hypoglycemic glucose concentration measurements that will occur interval time i;
compare the calculated $\chi^2$ to a $\chi^2$ value in a table based on a number of degrees of freedom for each of the time slot intervals i;
determine that at least one of the time slot intervals are statistically significantly different if the calculated $\chi^2$ is greater than the $\chi^2$ value of the table; and
calculating $L_{i,pre}$ and $L_{i,pre}'$ using estimation equations comprises:

$$L_{i,pre} = \frac{\sum_{i=1}^{n} L_i}{\sum_{i=1}^{n} N_i} * N_i$$

and $$L'_{i,pre} = \frac{\sum_{i=1}^{n} L'_i}{\sum_{i=1}^{n} N_i} * N_i$$

where $N_i$ represents the total number of glucose concentration measurements performed during time interval i.

7. The system of claim 6, in which the controller is further configured to:
identify one of the time slot intervals as being statistically significantly different with a Z test.

8. The system of claim 7, in which the controller is further configured to:
calculate $Z_i$ using a Z test, the Z test comprising:

$$Z_i = \frac{(L_i - L_{i,pre})}{SE_i}$$

where $Z_i$ represents a Z test at a particular time slot interval i and $SE_i$ represents a standard error for a particular time slot interval i;
compare a calculated $Z_i$ to a Z value in a table; and
identify that one of the time slot intervals is statistically significantly different if the calculated $Z_i$ is greater than the Z test; and
annunciate the one of the time slot intervals.

9. The system of claim 8, wherein the Z test includes a threshold of about one to about two.

10. The system of claim 9, in which the controller is configured to:
calculate $SE_i$, using a standard error equation comprising:

$$SE_i = \sqrt{\frac{1}{N_i} * L_{i,pre} * (N_i - L_{i,pre})}$$

11. A method of managing diabetes risks of a subject, the method comprising:
determining at least one of certain trends in a time of a day for glucose measurements with at least one glucose monitor and a controller in communication with the at least one glucose monitor, the controller including a microprocessor and configured to receive or transmit glucose data representative of glucose levels measured by the glucose monitor, and the determining comprising:
performing a plurality of glucose measurements over a predetermined time period with the glucose monitor;
identifying, with the microprocessor, from the plurality of glucose measurements whether the glucose data includes or does not include:
(a) an overall trend of the glucose data, the overall trend having:
(1) a minimum number of glucose measurements;
(2) a minimum number of glucose measurements that have values in the above a target range, below a target range, or in-range category in the time slot; and
(3) a percentage of glucose measurements in the timeslot being greater than a minimum threshold;

(b) a significant trend in which such significant trend is statistically and significantly different than the trends observed in other timeslots and a chi-squared test is used to determine if a particular time slot of the time slots is statistically significantly different than other time slots; the statistical test being based on a percentage of hypoglycemic incidence per the time slot interval and a predicted percentage of hypoglycemic incidence per the time slot interval; and (c) a minor trend of the glucose data, the minor trend having a minimum number of glucose measurements within a specified number of days that have values above a target range, below a target range, or in-range category in the time slot and all of the glucose measurements in the minimum number must be within a specified number of hours of each other in the event the identifying step indicates the glucose data includes both of the overall trend and the minor trend but not the significant trend:

using at least one of the overall trend or the minor trend to calculate an amount of a drug to be delivered to the subject by a drug delivery device in communication with the controller, wherein the amount of the drug is calculated to manage diabetes risks of the subject; and delivering, by the drug delivery device, the calculated amount of the drug to the subject.

12. The method of claim 11, wherein a chi-squared test is used to determine if any of the time slots is statistically significantly different from other time slots.

13. The method of claim 12, wherein the chi-squared test comprises a confidence level of about 90%.

14. The method of claim 13, wherein the number of glucose measurements is greater than about 14.

15. The method of claim 13, further comprising:
calculating a chi-squared $\chi^2$ using the following:

$$\chi^2 = \sum_{i=1}^{n} \frac{(L_i - L_{i,pre})^2}{L_{i,pre}} + \sum_{i=1}^{n} \frac{(L'_i - L'_{i,pre})^2}{L'_{i,pre}}$$

where $\chi^2$=chi-squared, i represents a particular time slot interval, n is a total number of time slot intervals, $L_i$ is a number of substantially hypoglycemic glucose concentration measurements that occur during time slot interval i, $L_{i,pre}$ is a predicted number of substantially hypoglycemic glucose concentration measurements that will occur during time slot interval i, and $L_{i,pre}'$ is a predicted number of non-hypoglycemic glucose concentration measurements that will occur interval time i;

comparing a calculated $\chi^2$ to a $\chi^2$ value in a table based on a number of degrees of freedom for each of the time slot intervals i; and determining that at least one of the time slot intervals are statistically significantly different if the calculated $\chi^2$ is greater than the $\chi^2$ value on the table.

16. The method of claim 15, further comprising:
calculating $L_{i,pre}$ and $L_{i,pre}'$ using estimation equations comprising:

$$L_{i,pre} = \frac{\sum_{i=1}^{n} L_i}{\sum_{i=1}^{n} N_i} * N_i$$

and $$L'_{i,pre} = \frac{\sum_{i=1}^{n} L'_i}{\sum_{i=1}^{n} N_i} * N_i$$

where $N_i$ represents the total number of glucose concentration measurements performed during time interval i.

17. The method of claim 13, further comprising: identifying one of the time slot intervals as being statistically significantly different using a Z test.

18. The method of claim 17, in which the Z test comprises:

$$Z_i = \frac{(L_i - L_{i,pre})}{SE_i}$$

where $Z_i$ represents a Z test at a particular time slot interval i and $SE_i$ represents a standard error for a particular time slot interval i; and the method further comprising:

comparing a calculated $Z_i$ to a Z value in a table; and
identifying that one of the time slot intervals is statistically significantly different if the calculated $Z_i$ is greater than the Z test.

19. The method of claim 18, wherein the Z test includes a threshold of about one and calculating $SE_i$, using a standard error equation comprising:

$$SE_i = \sqrt{\frac{1}{N_i} * L_{i,pre} * (N_i - L_{i,pre})} .$$

* * * * *

UNITED STATES PATENT AND TRADEMARK OFFICE
CERTIFICATE OF CORRECTION

PATENT NO. : 9,592,002 B2
APPLICATION NO. : 13/624733
DATED : March 14, 2017
INVENTOR(S) : Thomas Schaible Page 1 of 1

It is certified that error appears in the above-identified patent and that said Letters Patent is hereby corrected as shown below:

Claim 2:
Column 17
Line 10, please change "being below the target range, 70% being within the target" to --being below the target range, and 70% being within the target--

Claim 6:
Column 17
Line 58, please change "comprises:" to --comprising:--

Claim 8:
Column 18
Line 27, please change "compare a calculated $Z_i$ to a $Z$ value in a table; and" to --compare a calculated $Z_i$ to a $Z$ value in a table;--

Claim 12:
Column 19
Line 30, please change "The method of claim 11, wherein a chi-squared test is" to --The method of claim 11, wherein the chi-squared test is--

Signed and Sealed this
Fifteenth Day of May, 2018

Andrei Iancu
*Director of the United States Patent and Trademark Office*